United States Patent [19]
Eilender et al.

[11] Patent Number: 4,959,059
[45] Date of Patent: Sep. 25, 1990

[54] LOW FRICTION MULTILAYER PAD

[75] Inventors: Kasriel Eilender, New York; Mille Stand, Croton-on-Hudson, both of N.Y.

[73] Assignee: Senecare Enterprises, Inc., New York, N.Y.

[21] Appl. No.: 297,977

[22] Filed: Jan. 17, 1989

[51] Int. Cl.$^5$ ............................................... A61F 13/16
[52] U.S. Cl. ................................. 604/358; 604/378; 604/382
[58] Field of Search ................ 128/889; 604/358, 363, 604/364, 378, 382

[56] References Cited

U.S. PATENT DOCUMENTS

| | | | |
|---|---|---|---|
| 3,670,731 | 6/1972 | Harmon | 604/364 |
| 3,804,092 | 4/1974 | Tunc | 604/364 |
| 4,077,410 | 3/1978 | Butterworth et al. | 604/382 |
| 4,519,798 | 5/1985 | Dinius | 604/358 |
| 4,572,174 | 2/1986 | Eilender et al. | 128/889 |
| 4,772,281 | 9/1989 | Armstead | 604/358 |
| 4,875,492 | 10/1989 | Mitchell et al. | 604/378 |

*Primary Examiner*—Randall L. Green
*Assistant Examiner*—Gary Jackson
*Attorney, Agent, or Firm*—Jacob B. Burke

[57] ABSTRACT

This invention involves a multilayer low friction ambulatory pad for treating or preventing bedsores and pressure sores, and for managing fluids discharged from a person's body. The pad may have the form of a diaper with panels fittable to a person's body. The pad has a first slippery nonporous layer on which is a moisture absorbent second layer. A slippery, thin, porous third layer is on the second layer. The three layers are peripherally bonded to form a nonpenable seam which permits unbonded areas of the layers to slide slightly with respect to each other. The third layer may be sprayed with a filmy, dry, slippery fourth layer. A fifth layer of lubricating material which may be a microencapsulated lubricant or a free lubricant is applied to the third and fourth layers to form a very slippery top surface. The fourth and fifth layers do not clog the pores of the third layer to pass air and fluids to the absorbent second layer. In other pads, the absorbent layer is omitted. All pads can be shaped to fit various portions of a person's body to which the pads can be attached. The pads can be discarded after a single use.

18 Claims, 2 Drawing Sheets

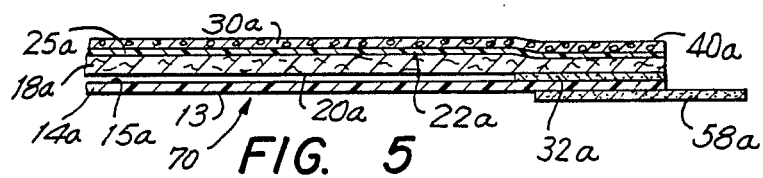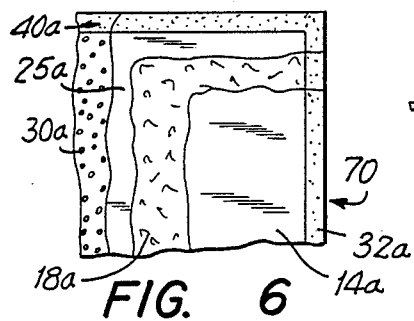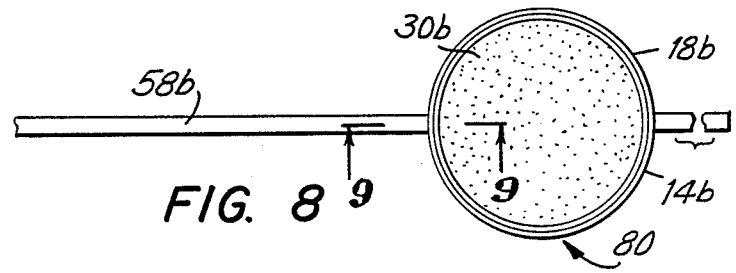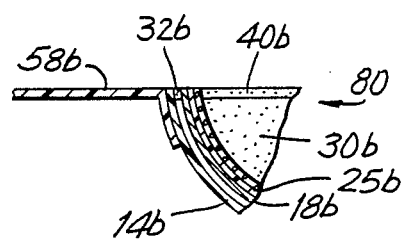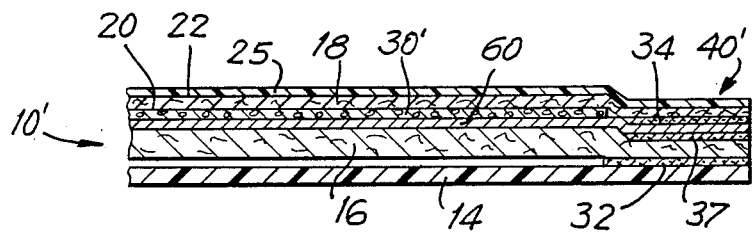

LOW FRICTION MULTILAYER PAD

BACKGROUND OF THE INVENTION

1. Field of the Invention

This invention concerns an improved low friction multilayer ambulatory pad for reducing or preventing bedsores, pressure sores, decubitous ulcers and similar lesions caused by pressure and friction applied to a person's body; and for managing fluids discharged from the body of a person such as a geriatric patient who is bedridden, confined to a wheelchair, or is ambulatory.

2. Description of the Prior Art

In our prior U.S. Pat. No. 4,572,174 which issued Feb. 25, 1986, we disclosed a bed pad structure intended to relieve the pressure, friction, and shear forces which are now recognized as principal causes of bedsores, pressure sores and decubitus ulcers in bedridden and chair ridden patients. We disclosed a low friction bed pad structure having a pouch portion between a woven fabric upper porous sheet and a lower flexible nonporous sheet. The pouch portion permitted insertion and removal of a lubricated sheet which exuded lubricant that seeped through the pores in the upper sheet to a patient's body when it applied pressure to the pad being held stationary on a bed, to reduce friction between the patient's body and the bed or other supporting surface to which the pad was attached.

The prior pad has proven generally successful, but experience has revealed it has some shortcomings, such as the following:

1. The procedure for inserting and removing the prelubricated sheets is messy and laborious.
2. The pad with lubricated insert removed must be thoroughly washed and sterilized before the pad can be reused.
3. The pad is made of relatively expensive materials which make the pad too costly to discard after a single use.
4. It is necessary to keep an adequate stock or supply of lubricated insert sheets on hand at all times; and this creates storage and inventory problems.
5. The prior pads are intended for use by bedridden patients and are not wearable by ambulatory patients who move frequently from bed to wheel chair to examination and treatment tables, etc. and back again.
6. There is a tendency for the loose insert sheets in use to move, migrate and bunch up inside the pouch portions of the pads.
7. The large bed pads are not adapted for application to a limited area of a patient's body, i.e. restricted, for example, to a patient's heels, elbows, head, shoulders, or other body part.
8. Careless or inept handling by attendants of lubricated inserts removed from pads used by seriously infected patients, can cause spread of infectious diseases.
9. The prior pads do not absorb material quantities of discharged body fluids such as perspiration, urine, blood, pus, etc.
10. Where there are pre-existing infections, the occurrence of bedsores in the presence of frequent urine discharges aggravates the condition and causes progressively more serious medical problems.

BRIEF DESCRIPTION OF THE INVENTION

It is a principal object of the present invention to provide an improved low friction multilayer pad or pads which have greater versatility and utility than prior low friction pads heretofore used for treating bedsores; and which are capable of managing discharged body fluids. Another object is to provide improved low friction pads which overcome the above mentioned and other difficulties and disadvantages encountered with prior low friction pads.

According to the invention there is provided a novel multilayered pad which can serve as a diaper or other low friction medium. The new pad has no pouch portion for a lubricated insert as heretofore used. The new pad has a bottom first layer made of thin, flexible, lightweight, strong, nonporous, slippery plastic material such as polyethylene. On this layer is secured an intermediate second layer made of porous, hydrophilic, highly liquid-absorbent, fibrous material which may be cellulose fibers. On the second layer is an upper third layer made of nonwoven, smooth, low friction, fibrous material. The three layers are attached to each other only at the registering outer edges of the layers in a suitable, permanent manner, as by gluing. The attachment extends all around the periphery of the pad without interruption to effect a complete seal. This construction securely anchors the layers in place with respect to each other while permitting limited frictionless sliding motion between the unattached inner portions of the layers. The external or top surface of the upper third layer is coated with a thin fourth layer or film composed of a dry, slippery substance such as polytetrafluoroethylene, to reduce further the coefficient of friction of the upper third layer. The fourth layer is so thin and so sparingly applied that it does not clog the pores of the nonwoven, porous third layer. On the fourth layer is applied a fifth layer composed of microencapsulated lubricant. The top fifth layer is dry to touch. This layer adheres to the third and fourth porous layers. The top layer penetrates the porous third layer to a negligible extent leaving the pores of the third layer unclogged so that they can pass body fluids therethrough to the adjacent, underlying moisture absorbent second layer. When body pressure is applied to the multilayered pad between a person's body and a supporting surface, the microcapsules break and exude their lubricant which renders the top of the pad very slippery and reduces the coefficient of friction of the pad to minimum magnitude, and increases the antifriction properties of the pad to a greater extent than is achievable by prior low friction multilayer pads.

In a modification of the invention, the lubrication coating can be a very thin layer of free medicated ointment. This does not clog the pores of the nonwoven third layer. The intermediate second layer freely takes up and absorbs all body discharged liquid which seeps through the porous upper third layer. Each of the five layers of the pad has antifriction properties, so that collectively they provide absolutely minimum resistance to shear forces and reduce the coefficient of friction of the pad to minimum magnitude. The lower three layers can slide to a limited extent with respect to each other, so that overall, the least possible friction can occur between a moving person's body and a supporting surface such as a bed, table, chair, treatment appliance, etc.

In a further modification, the multilayered pad can be made with only four layers, namely, the top or external lubrication layer, the dry, slippery low-friction layer or film, the porous, smooth, nonwoven fabric layer, and the nonporous bottom layer. The last named two layers are attached together by a continuous peripheral glued joint. The moisture absorbent layer used in the five-layer pad is omitted. The four-layer pad will have only limited moisture retention properties. The new multilayer pads afford the following advantages among others:

1. They are very light in weight, easy to handle, and non-messy at all times.

2. They are relatively inexpensive to manufacture, so that they can be discarded after a single use or whenever they become soiled.

3. Since the pads are intended for one-time usage, the dangers of spread of infectious diseases from usage, handling, storage, laundering, and reuse of pads, are avoided.

4. The new pads can be made in large or small sizes to cover an entire bed or table, or to cover any body part for stationary or ambulatory use.

5. The pads can be made in flat form or preshaped to fit any body part such as a person's head, shoulders, elbow, hip, heel, etc. with straps, tabs or other attachment means provided removably securing the pads to the bodies of person's using the pads.

6. The pads can be made up as preshaped diapers for adults suffering from incontinence of urine, to take up urine and other fluid discharges; and at the same time the new pads will be effective to reduce the incidence of bedsores, to ward off infections, and to facilitate healing of the sores.

7. The pads can provide effective means for collecting and retaining fluids discharged from any part of a person's body to which the pads are applied.

8. In all cases, the new pads will prevent the occurrence of bedsores, pressure sores and decubitus ulcers, and/or will reduce the severity of any sores which may occur. Also, the pads will accelerate healing of new or preexisting bedsores, pressure sores, and ulcers.

The above listed and other objects and advantages of the invention will become apparent from the following detailed description of the invention, taken in conjunction with the drawings, wherein:

BRIEF DESCRIPTION OF THE DRAWINGS

FIG. 5 is an enlarged fragmentary cross sectional view taken on line 5—5 of FIG. 4.

FIG. 6 is an enlarged fragmentary plan view of a portion of the pad shown in FIG. 4, parts being removed to show the multiple layer structure.

FIG. 7 is a side view of a bowl shaped pad embodying the invention, parts of attachment straps being omitted.

FIG. 8 is a plan view of the pad of FIG. 7, parts being omitted.

FIG. 9 is an enlarged fragmentary cross sectional view taken on line 9—9 of FIG. 8.

FIG. 10 is a cross sectional view similar to FIG. 2 of another multilayer pad.

DESCRIPTION OF THE PREFERRED EMBODIMENTS

Figure 1:
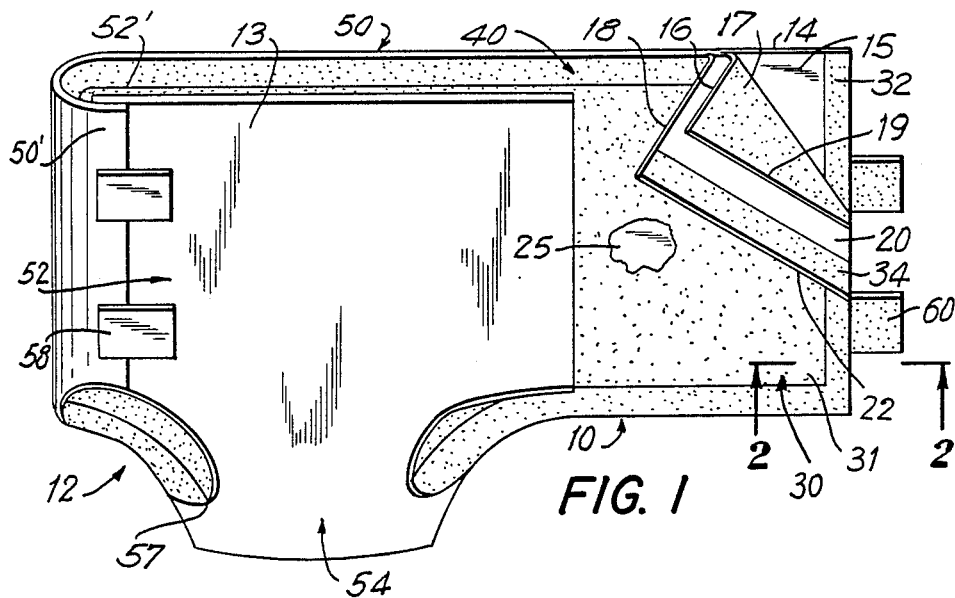
FIG. 1 is an oblique plan view of a multilayer pad in the form of a diaper, embodying the invention, parts being removed.
Figure 2:
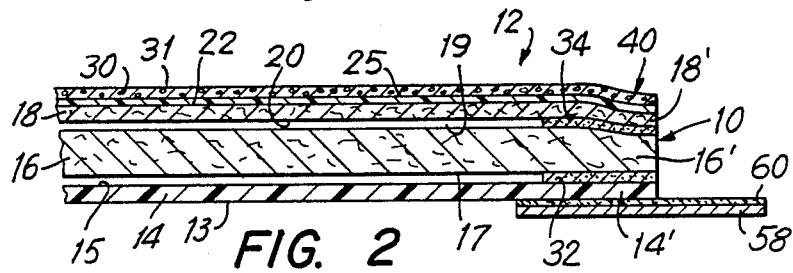
FIG. 2 is an enlarged fragmentary cross sectional view taken on line 2—2 of FIG. 1.
Figure 3:
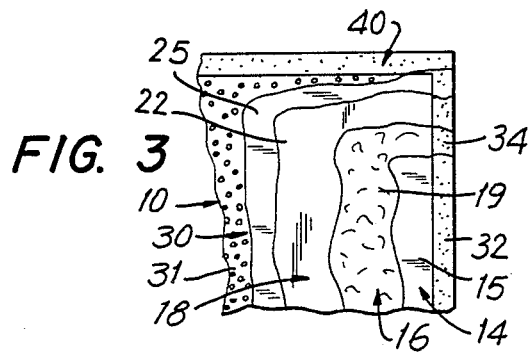
FIG. 3 is an enlarged fragmentary plan view of a portion of the pad of FIG. 1, parts being removed to show the multiple layer structure.

Referring now to FIGS. 1, 2 and 3, there is shown a five-layer pad 10 made in the form of a diaper 12 adapted for use by an adult person. The pad 10 has a bottom, outer first layer 14 made of a nonporous, flexible, moistureproof, plastic material such as polyethylene. This thin backing layer prevents moisture from seeping through the pad and thus servest o protect a user's clothing, bedding, furniture, etc. Layer 14 contacts a supporting surface such as a bed, table, chair, treatment device, etc. when the pad is in use. A preferred thickness for layer 14 is about 1.0 to 1.5 mils. On top surface 15 of backing layer 14 is a fibrous second layer 16 preferably made of nonwoven, porous cellulose fibers. This layer is very hydrophilic, i.e. it is highly absorbent of liquids. It takes up and holds urine, blood, pus, perspiration, and other fluids discharged from the user's body. A suitable weight for this material is about one ounce per square yard. The bottom surface 17 of layer 16 faces upper surface 15 of layer 14.

On upper surface 19 of the second layer 16 is a thin, porous third layer 18 preferably made of nonwoven, synthetic fibers such as polyester and/or rayon. The thin, flexible, porous layer 18 is very strong and smooth. The layer 18 may be about 0.8 to 1.0 mils thick. The lower surface 20 of layer 18 faces surface 19 of layer 16. Layers 14 and 18 present smooth, low friction, sliding surfaces 15 and 20 to the adjacent smooth, low friction surfaces 17 and 19 of layers 16 and 18. The porosity of layers 16 and 18 is an important feature of the invention because in addition to admitting moisture, the pores in these layers freely admit air to prevent the layers 14, 16 and 18 from sticking to each other by suction. This enhances the low friction properties of pad 10.

On the upper surface 22 of third layer 18 is a very thin, dry, slippery fourth layer 25 made of a material such as a silicone, polytetrafluorethylene, or the like. The material is applied by spraying or otherwise to form a very thin film about 0.05 to 0.1 mills thick. This film will effectively reduce the low coefficient of friction of surface layer 22 to about 0.01. It will be applied sparingly so as not to clog the pores of the third layer 18. About 1.0 to 5.0 grams of sprayed material per square meter of layer 18 will generally be sufficient for forming slippery layer 25 on upper surface 22 of layer 18. On top of fourth layer 25 and on the third layer 18 is a thin low friction coating 30 preferably made of silicone, polytetrafluorethylene, an oil such as jojoba, or other lubricant in droplet form encapsulated in tiny frangible plastic bubbles or capsules. The microscopically small capsules can be as small as 0.01 millimeters (about 10 microns). The layer 30 of encapsulated lubricant is dry to touch. When heat and pressure of a person's body as well as shear forces are applied to pad 10 resting on a supporting surface or against it, the microcapsules break and release the encapsulated lubricant. This forms a fluid, slippery surface on layers 25 and 18 and reduces the coefficient of friction of the top of the pad to infinitesimally small magnitude, for example, to less than 0.01. The microcapsules can be made of natural or synthetic polymers. The lubrication layer 25 can be applied by rolling, spraying, etc. Layer 30 will have good bonding to the slippery layer 25 and to the porous layer 18 without clogging the pores in layer 18, so that liquids and air can readily penetrate layer 18 to reach layer 16, where the liquid will be fully absorbed by layer 16.

The lower three layers 14, 16 and 18 are secured together only at their registering abutted outer edges 14', 16', 18' by narrow adhesive stripes 32, 34. The adhesive can be hot melt glue or other adhesive. The entire lengths of the registering edges of the three layers are pressed and secured together to form a continuous, endless, permanent seam. This seam is an important feature of of the invention because it permits the remainders of layers 14, 16 and 18 to shift slightly in their planes with respect to each other, with respect to a supporting surface, and with respect to the user's body. Thus when pad 10 is in place for use attached to a person's body, there will be present at least eight cooperating low friction surfaces. Slippery surfaces 15 and 17 face each other. Slippery surfaces 19 and 20 face each other. Slippery surface 31 of lubrication layer 30 faces the person's body, and slides on slippery layer 25 and on slippery surface 22 of layer 18; and slippery surface 13 of layer 14 can slide on whatever surface supports the weight of the person's body. The antifriction surfaces cooperate to produce a cumulative infinitesimally small coefficient of friction, so that shifting movements of the user with respect to the supporting surface encounter substantially no resisting force. The porosity of layers 16 and 18 prevents the three layers 14, 16 and 18 from sticking to each other by preventing suction. Thus bedsores and pressure sores which are the end results of continual pressure and repeated sliding friction and shear forces on the skin surfaces of the user are prevented to a greater extent than is possible by any prior low friction pad; and healing of any existing pressure sores and pressure ulcers is facilitated.

The diaper 12 is so shaped that it will snugly cover the crotch, lower back and abdomen of an adult person. The diaper body has a long, generally rectangular upper or back panel 50 which is about twice as long as it is wide and sufficiently long to wrap around the body and sides of a person's body with end edges 50' overlapping the person's abdomen. A lower generally panel 52 for covering the abdomen of the person's body is provided. Panel 52 is about one half the length of panel 50, but it can be larger for stout persons, is connected by a narrower integral crotch piece or panel 54 to panel 50. The three panels 50, 52, 54 have adjacent edge portions 57 which are curved to define leg openings adapted to fit snugly around the legs of the user of the diaper 12 when edges 50' of panel 50 overlap edges 52' of panel 52 as shown in FIG. 1, while crotch panel 54 extends under and around the person's crotch. At the outer edges 50' of panel 50 are tabs 58 having adhesive sides 60 facing forwardly when the diaper is open. These tabs hold the diaper closed by engaging on panel 52 and cooperate with the three panels to hold the diaper 12 in place on the body of the wearer while he or she moves about.

The panels 50 and 52 need not be precisely rectangular as shown in FIG. 1. The panels can have rounded corners, curved upper and lower edges, or other suitable shapes to conform to the body of the user. In all forms of the diaper they must be arranged so that the three panels can be secured in place on the user's body by any suitable means, while the user moves about.

Figure 4:
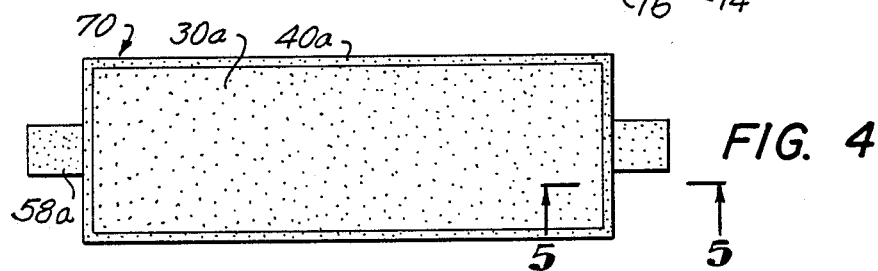
FIG. 4 is a plan view of a flat rectangular pad embodying a modification of the invention.

In FIGS. 4, 5 and 6 are shown views of a flat, rectangular multiple layered pad 70. This pad is similar in construction to pad 10 and corresponding parts have identical sublettered numbers. In pad 70 the moisture absorbent layer 16 of pad 10 is omitted. Bottom nonporous layer 14a is overlaid with upper porous layer 18a whose top surface is covered with slippery layer 25 and encapsulated lubrication layer 30a. Low friction surface 15a of layer 14a faces low friction surface 20a of layer 18a. The two layers can slide with respect to each other because the pores in layer 18a admit air to prevent suction. The two layers are peripherally joined at their registering outer edges by seam 40a extending continuously all around the edges of the layers and permanently secured by adhesive film 32a. Pad 70 can be smaller or larger than pad 10. It can be used flat on a bed or it can be wrapped around a part of a person's body. It can be applied substantially flat to a person's back or curved around shoulders, hips or other body parts. Adhesive tabs 58a at edges of pad 70 can be suitably coated with adhesive to secure the wrapped or flat pad removably in place on a person's body. Thus pad 70 in use can be ambulatory or stationary to rest on a bed, chair, or other supporting surface.

It is possible to make the four-layer pad 70 and five-layer pad 10 in different shapes than shown in FIGS. 1 and 4, and in different sizes to conform to flat or curved parts of the user's body. For example, in FIGS. 7, 8 and 9 is shown a four-layer pad have a bowl, cup or cap shape, expecially adapted for application to a person's head, heel, elbow, shoulder or other curved body part. Pad 80 has a nonporous, slippery outer first layer 14b lined on its inner side with porous, fibrous, low friction layer 18b. The two layers 14b and 18b are bonded together all around their peripheries by adhesive 32b forming seam 40b. The upper side of layer 18b is coated with dry, thin, slippery, filmy, nonclogging layer 25b. Lubrication layer 30b covers layers 25b and 18b. Long straps 58b are secured to opposite points at the periphery of pad 80 enable the pad to be tied in place covering a curved portion of a person's body to protect it from developing pressure induced and friction induced sores. Pad 80 is thus ambulatory but remains in place where it is attached whenever and whereever the wearer stands, sits and lies down. The moisture absorbent layer 16 employed in pad 10 is ommited from pad 80, but if a moisture absorbent layer is needed in pad 80 as well as in pad 70, it can be provided like layer 16 in pad 10, positioned between the outer or bottom nonporous layer 14a or 14b and the porous layer 18a or 18b in a manner similar to that shown in FIGS. 1, 2 and 3.

It is possible to apply a very thin layer of a free lubricant in place of the encapsulated lubrication layer 30, 30a or 30b, if desired. For example, the layer of free lubricant can have a lanolin, aloe vera, cocoa butter, or other free fluid base alone or mixed with a suitable antiseptic or other medicinal ingredient. The free lubricant can be a medicated ointment. The free lubricant will have a low enough viscosity so that it can be sparingly applied to avoid clogging the pores in layers 18, 18a and 18b. The free lubricant will form a very slippery surface 31 against the body of the user of the pad. A suitable application of lubricant may be about 15.0 to 25.0 grams per square meter of covered surface. Upon application of pressure to the pad with sliding movement of the user's body, the fluid lubricating layer will offer infinitesimally low friction to the moving skin surface. The lubricating layer will cooperate with the other layers to reduce resistance of the pad to sliding movements on the supporting surface, to negligibly small magnitudes.

When a free fluid lubricant is applied to the pad, it may be desired that the top surface facing the user be normally dry to touch prior to use of the pad. This dryness can be achieved as shown in pad 10' of FIG. 10, by applying the lubricating layer 30' as a thin nonclogging fluid film to the underside 20 of porous layer 18, instead of on the upper side 22 and on dry, filmy, slippery layer 25. When pressure and heat are applied by a person's body to a supporting surface with the multilayer pad disposed therebetween, the fluid lubricant 30' will pass through the pores in layer 18 to form the very slippery surface 31 indicated in FIGS. 2 and 3 on layer 25, and on the upper side 22 of layer 18. Since at this time both sides of porous layer 18 will be coated with the free fluid lubricant, friction and shear forces applied to the patient's body while on the pad will be minimized to attain a coefficient of friction as low as 0.01 or even lower.

Since the free fluid lubricant applied to the underside of the porous layer 18 will be very sparingly applied it will not clog the pores in this layer, so that any fluids discharged from the patient's body will pass freely through the pores in layer 18 to the moisture absorbent layer 16 for absorption thereby.

If it is desired to prevent the free fluid lubricant 30' applied to the underside of layer 18 from contacting the adjacent moisture absorbent layer 16, it is possible if necessary, to provide a very thin, dry, porous barrier or buffer sheet 60 between the porous layer 18 undercoated with free lubricant 30', and the moisture absorbent layer 16 as shown in FIG. 10. This barrier layer is preferably made of nonwoven, nonabsorbing, fibrous fabric material. Barrier layer 60 is porous enough to permit any body fluids passing through porous layer 18 to also pass to hydrophilic, absorbing layer 16. The porous barrier sheet 60 will be bonded in place in a nonremovable manner by adhesive 37 in peripheral seam 40'.

The dry, thin, slippery layer 25, 25a or 25b is very sparingly applied by lightly spraying or even misting it upon the porous layer 18, 18a or 18b to form a surface which is dry to touch. The dry lubricant layer may be about 4% by weight of the composite layers 18, 25, and the porous layer 18 may be about 96% by weight of the composite layers. The dry lubricant layer cooperates in a synergistic way with the applied lubricating layer 30 to enhance the slipperness of top surface 31; by this is meant that the reduction in the coefficient of friction of upper surface 22 of layer 18 is more than would normally be expected from use of filmy lubricant 25 plus lubricant 30 on layer 18.

It may be that the lubricating layer 30, 30a, 30b, or 30' in cooperation with slippery layer 18, 18a or 18b, is sufficiently slippery when very light pressures are applied to the multilayer pad 10, 70, 80, or 10', so the percentage by weight of dry lubricant layer 25, 25a or 25b can be reduced.

In multilayer pads intended for some applications, layer 16 can be bonded to layer 14 and/or to layer 18 at areas spaced inwardly of the peripheral seam 40 or 40', 40a or 40b, to limit shifting of the layers with respect to each other.

In all forms of the invention described, the pads will be effective instrumentalities to prevent development of bedsores, pressure sores, and decubitus ulcers, and to expedite healing of existing sores. All the low friction pads described are characterized by light weight and low manufacturing cost as well as low bulk and low material cost. Thus the pads are expendable and can be discarded at little expense after a single use. All the pads can be applied and used easily. No replacement of lubricated liners or inserts, laundering, or sterilizing is necessary. The new pads will be presterilized when manufactured and will thus economize in consumption of time and labor of nurses and other attendants. The pads can be supplied in compact, sterile packages. They will occupy minimun storage space and will have very long shelf life. The pads can be individually packaged in throw-away bags or envelopes; or for economy and convenience they can be packaged in bulk.

While we have disclosed a plurality of embodiments of the invention, these have been by way of example only. It will be understood that many modifications are possible without departing from the invention as defined in the following claims.

What is claimed is:

1. A pad for preventing and treating pressure sores on a person's body and for managing discharged body fluids, comprising:

an outer first layer formed of thin, nonporous, moistureproof, flexible sheet material having a smooth outer side for abutting a supporting surface, and having a smooth other side;

a second layer formed of soft, porous, moisture absorbent material superimposed on said other side of said first layer to absorb and retain said fluids;

a third layer formed of thin, porous, smooth, fibrous sheet material superimposed on said second layer for passing said fluids through pores in said third layer to said second layer for absorption thereby;

a fourth layer composed of dry, slippery material formed as an extremely thin filmy coating on said third layer, said coating having sufficient body to reduce the coefficient of friction of said third layer, and having sufficient thinness to leave said pores in said third layer unclogged to pass said fluids therethrough;

a fifth layer formed of lubricating material applied to said third and fourth layers and effective to provide a very slippery surface thereat to minimize sliding friction and shear forces between said person's body and said supporting surface, said fifth layer being so applied that said pores in said third layer remain unclogged so that said fluids can pass freely to and through said pores to said second layer for absorption thereby; and means nondetachably bonding together registering marginal areas of said first, second and third layers in a continuous seam all around their joined peripheries to allow limited sliding movement between unbonded areas of said layers, while said first, second, third, fourth and fifth layers cooperate to minimize sliding friction and shear forces between said person's body and said supporting surface with said pad disposed therebetween.

2. A pad as claimed in claim 1, wherein said third layer has an underside and an upper side, and wherein said lubricating material is composed of a free fluid lubricant applied to said underside of said third layer, so that said upper side of said third layer is normally dry to touch until said lubricant passes through said pores in said third layer when pressure is applied by said person's body to said pad against said supporting surface, to form a very slippery top surface for minimizing friction and shear forces thereat.

3. A pad as claimed in claim 2, further comprising a sixth layer in the form of a thin porous sheet interposed between said moisture absorbent second layer and said free fluid lubricant at said underside of said third layer to serve as a barrier for preventing said lubricant from contacting said second layer while permitting said body fluids passing through said third layer to reach said second layer for absorption thereby; and means bonding said sixth layer nonremovably in place between said second and said third layers.

4. A pad for preventing and treating pressure sores on a person's body, and for managing discharged body fluids, comprising:
   an outer first layer formed of thin, nonporous, moistureproof, flexible sheet material having a slippery outer side for abutting a supporting surface, and having a smooth other side;
   a second layer formed of soft, porous, moisture absorbent material superimposed on said other side of said first layer to absorb and retain said fluids;
   a third layer formed of thin, porous, slippery, low friction, fibrous sheet material superimposed on said second layer for passing said fluids through pores in said third layer to said second layer for absorption thereby;
   a fourth layer formed of lubricating material applied to said third layer and effective to reduce sliding friction and shear forces between said body and said supporting surface, said lubricating material being so applied that said pores remain unclogged so that said fluids can pass freely to and through said pores of said third layer to said second layer; and
   means nondetachably bonding together registering marginal edges of said first, second and third layers in a continuous seam all around their peripheries to allow limited sliding movements between unbonded areas of layers, while said first, second, third and fourth layers cooperate to minimize sliding friction and shear forces between said person's body and said supporting surface.

5. A pad as claimed in claim 4, wherein said layers are geometrically shaped to conform to areas of a person's body subject to development of pressure sores, and further comprising means for attaching said pad to said person's body, so that said pad remains in place covering said last named areas while said person moves about.

6. A pad as claimed in claim 4, wherein said lubricating material is composed of microscopically small, frangible capsules enclosing droplets of lubricant, so that said fourth layer is substantially dry to touch until said capsules are broken by pressure and heat applied by said person's body to said pad against said supporting surface, to release said lubricant from said capsules to form a very slippery top surface on said third layer.

7. A pad as claimed in claim 4, wherein said lubricating material is composed of a thin film of free lubricant.

8. A pad as claimed in claim 4, wherein said lubricating material is composed of dry, slippery material formed as an extremely thin filmy coating on said third layer to reduce the coefficient of friction of said third layer.

9. A pad as claimed in claim 4, wherein said third layer has an underside and an upper side, and wherein said lubricating material is composed of a free fluid lubricant applied to said underside of said third layer, so that said upper side of said third layer is normally dry to touch until said lubricant passes through said pores in said third layer when pressure is applied by said person's body to said pad against said supporting surface, to form a very slippery top surface for minimizing friction and shear forces thereat.

10. A pad as claimed in claim 9, further comprising a fifth layer in the form of a thin porous sheet interposed between said moisture absorbent second layer and said free fluid lubricant at said underside of said third layer to serve as a barrier for preventing said lubricant from contacting said second layer while permitting said body fluids passing through said third layer to reach said second layer for absorption thereby; and means bonding said fourth fifth layer nonremovably in place between said second and said third layers.

11. A pad as claimed in claim 4, wherein all of said layers are so shaped as to define a diaper for enclosing portions of said person's body subject to discharge of said fluids, said diaper comprising:
   an elongated first panel having a length sufficient to wrap around the back and sides of said person's body;
   a second panel shorter than said first panel to overlay said person's abdomen, with ends of said first panel overlapping ends of said second panel;
   a narrow crotch panel integral with and connecting said first and second panels; and
   means for detachably securing said ends of said first and second panels together with said crotch panel extending under and around said person's crotch, so that said diaper is held securely in place on said person's body while said person moves about.

12. A pad as claimed in claim 11, wherein said panels have curved adjacent end portions shaped to define openings for encircling legs of said person when said first and second panels are attached together on said person's body.

13. A pad for preventing and treating pressure sores on a person's body, comprising:
   a first layer formed of thin, slippery, nonporous, moistureproof, flexible sheet material having a smooth side for abutting a supporting surface, and having a smooth other side;
   a second layer formed of thin, porous, low friction, fibrous material superimposed on said other side of said first layer;
   a third layer composed of dry, slippery material forming an extremely thin film coating on said second layer with sufficient body to reduce the coefficient of friction of said second layer, but with sufficient thinness to leave pores in said second layer unclogged;
   a fourth layer formed of lubricating material applied to said second and third layers and effective to reduce sliding friction and shear forces between said person's body and said supporting surface while leaving pores in said second layer unclogged; and
   means nondetachably bonding together registering marginal areas of said first and second layers in a continuous seam all around their peripheries, to allow limited sliding movements between said first and second layers, while said first, second, third and fourth layers cooperate to minimize sliding friction and shear forces between said person's body and said supporting surface with said pad disposed therebetween.

14. A pad as claimed in claim 13, wherein said fourth layer is composed of microscopically small, frangible capsules which enclose droplets of a lubricant, so that said fourth layer is substantially dry to touch until said capsules are broken by pressure applied between said person's body and said supporting surface with said pad therebetween, to release said lubricant and form a slippery top surface on said second and third layers.

15. A pad as claimed in claim 13, wherein said fourth layer is composed of a very thin film of free lubricant.

16. A pad as claimed in claim 13, wherein said second layer has an underside and an upper side, and wherein said lubricating material is composed of a free fluid lubricant applied to said underside of said second layer so that said third layer and said upperside of said second layer are normally dry to touch until said lubricant passes through said pores in said second layer when pressure is applied by said person's body against said supporting surface with said pad disposed therebetween, to form a very slippery top surface to minimize friction and shear forces thereat.

17. A pad as claimed in claim 13, wherein all of said layers are geometrically shaped to conform to areas of a person's body subject to development of pressure sores.

18. A pad as claimed in claim 17, further comprising means for attaching said pad to said person's body, so that said pad remains in place covering said last named areas while said person moves about.

* * * * *